United States Patent
Ramachandran Nair et al.

(10) Patent No.: US 10,059,652 B2
(45) Date of Patent: Aug. 28, 2018

(54) HETEROGENEOUS CATALYSTS FOR THE TRANSESTERIFICATION OF AROMATIC ALCOHOLS; AND METHODS OF MAKING AND USE THEREOF

(71) Applicant: SABIC GLOBAL TECHNOLOGIES B.V., Bergen op Zoom (NL)

(72) Inventors: Balamurali Krishna Ramachandran Nair, Sugar Land, TX (US); Edouard Mamedov, Houston, TX (US); Pamela Lawyer-Harvey, Missouri City, TX (US); Neeta Kulkarni, Houston, TX (US); Jonathan Banke, Sugar Land, TX (US)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 27 days.

(21) Appl. No.: 14/914,421

(22) PCT Filed: Aug. 29, 2014

(86) PCT No.: PCT/US2014/053355
§ 371 (c)(1),
(2) Date: Feb. 25, 2016

(87) PCT Pub. No.: WO2015/031724
PCT Pub. Date: Mar. 5, 2015

(65) Prior Publication Data
US 2016/0207872 A1  Jul. 21, 2016

Related U.S. Application Data

(60) Provisional application No. 61/871,889, filed on Aug. 30, 2013, provisional application No. 61/871,888, filed on Aug. 30, 2013.

(51) Int. Cl.
| | | |
|---|---|---|
| *B01J 23/22* | (2006.01) | |
| *C07C 69/96* | (2006.01) | |
| *B01J 23/847* | (2006.01) | |
| *B01J 23/885* | (2006.01) | |
| *B01J 23/89* | (2006.01) | |
| *B01J 27/199* | (2006.01) | |
| *C07C 68/06* | (2006.01) | |
| *B01J 23/28* | (2006.01) | |
| *B01J 23/34* | (2006.01) | |
| *B01J 23/887* | (2006.01) | |
| *B01J 27/057* | (2006.01) | |
| *B01J 37/02* | (2006.01) | |
| *B01J 37/03* | (2006.01) | |

(52) U.S. Cl.
CPC .............. *C07C 69/96* (2013.01); *B01J 23/22* (2013.01); *B01J 23/28* (2013.01); *B01J 23/34* (2013.01); *B01J 23/8472* (2013.01); *B01J 23/885* (2013.01); *B01J 23/8877* (2013.01); *B01J 23/8993* (2013.01); *B01J 27/0576* (2013.01); *B01J 27/199* (2013.01); *B01J 37/0213* (2013.01); *B01J 37/0236* (2013.01); *B01J 37/031* (2013.01); *C07C 68/06* (2013.01); *B01J 2523/00* (2013.01)

(58) Field of Classification Search
CPC .. C07C 69/66; B01J 23/22; B01J 23/28; B01J 23/34
See application file for complete search history.

(56) References Cited

U.S. PATENT DOCUMENTS

| | | |
|---|---|---|
| 3,773,828 A | 11/1973 | Kadowaki et al. |
| 4,339,355 A | 7/1982 | Decker et al. |
| 5,166,393 A | 11/1992 | Fukuoka et al. |
| 5,344,954 A | 9/1994 | Schon et al. |
| 5,354,923 A | 10/1994 | Schon et al. |
| 5,565,605 A | 10/1996 | Tsuneki et al. |
| 5,907,056 A | 5/1999 | Karim et al. |
| 6,030,920 A | 2/2000 | Karim et al. |
| 7,378,540 B2 * | 5/2008 | Ryu ................... B01J 23/20 558/274 |
| 8,415,495 B2 | 4/2013 | Ryu |
| 8,697,596 B2 | 4/2014 | Kaduk et al. |
| 2008/0132404 A1 | 6/2008 | Ryu |
| 2009/0305880 A1 | 12/2009 | Ryu |

FOREIGN PATENT DOCUMENTS

| | | |
|---|---|---|
| CN | 1803282 A | 7/2006 |
| CN | 1915504 A | 2/2007 |
| EP | 0294845 A1 | 12/1988 |
| EP | 1500671 A1 | 1/2005 |

(Continued)

OTHER PUBLICATIONS

Mitran et al., "Semiconductive properties of Mo—V—M—O (M=Zn, Ni, Cu, Sb) oxides, catalysts for isobutane oxidehydrogenation," Reac Kinet Mech Cat (2010) 99: 135-142.
English Abstract of CN1803282(B); Date of Publication: Jul. 19, 2006; 1 Page.
English Abstract of CN1915504; Date of Publication: Feb. 21, 2007; 1 Page.
English Abstract of JPH08231472; Date of Publication: Sep. 10, 1996; 1 Page.
Huajun et al.; "A Heterogeneous Catalyst for the Transesterification of Dimethyl Carbonate and Phenol to Form Diphenyl Carbonate"; Chinese Journal of Catalysis; vol. 27; Issue 1; Jan. 2006; pp. 7-8.
International Preliminary Report on Patentability for International Application No. PCT/US2014/053355; International Filing Date: Aug. 29, 2014; dated Jan. 28, 2016; 7 Pages.

(Continued)

*Primary Examiner* — Pancham Bakshi
(74) *Attorney, Agent, or Firm* — Cantor Colburn LLP (57) ABSTRACT

Disclosed herein are new mixed metal oxide catalysts suitable as heterogeneous catalysts for catalyzing the transesterification process of aromatic alcohols with a dialkyl carbonate to form aromatic carbonates. The heterogeneous catalyst comprises a combination of two, three, four, or more oxides of Mo, V, Nb, Ce, Cu, Sn, or an element selected from Group IA or Group IIA of the periodic table.

14 Claims, 3 Drawing Sheets

(56) References Cited

FOREIGN PATENT DOCUMENTS

| EP | 2143750 A1 | 1/2005 |
|---|---|---|
| EP | 2248841 A1 | 11/2010 |
| JP | 54125617 A | 9/1979 |
| JP | 08231472 A | 9/1996 |

OTHER PUBLICATIONS

International Search Report for International Application No. PCT/US2014/053355; International Filing Date: August 9, 2014; dated Nov. 6, 2014; 5 Pages JP54125617; Date of Publication Sep. 29, 1979; English Abstract; 1 page.

Kim et al.; "A new process for the synthesis of diphenyl carbonate from dimethyl carbonate and phenol over heterogeneous catalysts"; Catalysis Letters 59; 1999; pp. 83-88.

Tong et al.; "Transesterification of dimethyl carbonate with phenol to diphenyl carbonate over V2O5 catalyst"; Journal of Molecular Catalysis A: Chemical 268; 2007; pp. 120-126.

Tong et al.; "V—Cu Composite Oxide Catalyst for Transesterification of Dimethy Carbonate with Phenol to Diphenyl carbonate"; Chinese Journal of Catalysis; vol. 28; Issue 3; Mar. 2007; pp. 190-192.

Wang et al.; "Pyroaurite as an active, reusable and environmentally benign catalyst in synthesis of diphenyl carbonate by transesterification"; Catalysis Communications 11; 2009; pp. 202-205.

Weiqing et al.; "Synthesis of diphenyl carbonate by transesterification over lead and zinc double oxide catalyst"; Applied Catalysis A; General 260; 2004; pp. 19-24.

Written Opinion of the International Searching Authority for International Application No. PCT/US2014/053355; International Filing Date: Aug. 29, 2014; dated Nov. 6, 2014; 5 Pages.

Zhang, Y. et al. "Silica-supported MoVNbO Complex Oxide Catalyst for Low-Temperature Oxidation of Ethane to Acetic acid", Chinese Journal of Catalysis, Aug. 2005, vol. 26, No. 8, pp. 719-723.

\* cited by examiner

HETEROGENEOUS CATALYSTS FOR THE TRANSESTERIFICATION OF AROMATIC ALCOHOLS; AND METHODS OF MAKING AND USE THEREOF

CROSS REFERENCE TO RELATED APPLICATIONS

This application is a National Stage application of PCT/US2014/053355, filed Aug. 29, 2014, which claims priority to U.S. Application No. 61/871,889, filed Aug. 30, 2013, and to U.S. Application No. 61/871,888, filed Aug. 30, 2013, which are incorporated by reference in their entirety herein.

BACKGROUND

Aromatic carbonates such as diphenyl carbonate (DPC) are common reagents in the formation of polycarbonates. One of the most important processes to prepare DPC is the transesterification of a dialkyl carbonate. For example the transesterification of diethyl carbonate and phenol to form intermediate phenylethyl carbonate which can then be subjected to another transesterification with phenol or a disproportionation reaction to DPC. Another example is the transesterification of (I) dimethyl carbonate (DMC) and phenol (PhOH) to form intermediate phenyl methyl carbonate (PMC) which can then be subjected to another transesterification with phenol (II) or a disproportionation reaction (III) to DPC as shown in the following schemes.

Homogeneous catalysts are known to be used in the transesterification of aromatic hydroxy compounds (also referred to as aromatic alcohols) and dialkyl carbonates to produce aromatic carbonates. These catalysts are corrosive and need to be dissolved in the reactants. Additionally, these catalysts have to be separated from the reactor effluent before further processing of the final product. Although a large portion of the homogeneous catalyst can be recycled, a certain amount of fresh catalyst must be supplied continuously to the reaction system for an industrial process. This results in a complicated and energy intensive industrial process. In addition, trace amounts of homogeneous catalyst ending up in the product affects the properties of the resulting polymeric material rendering it unsuitable for certain applications.

There have been a few reports of heterogeneous transesterification catalysts, although their activity and selectivity are not high enough to be attractive for industrial application.

There remains a need in the art for new transesterification catalysts that are improved above the known homogeneous catalysts and the heterogeneous catalysts, particularly in activity and selectivity.

BRIEF DESCRIPTION

In an embodiment, a heterogeneous catalyst comprises a mixed metal oxide according to Formula (A) $Mo_aV_bNb_cQ_dO_x$ (A), wherein Q is Ce, Cu, Sn, an element selected from Group IA of the periodic table (e.g. Na, K or Cs), or an element selected from Group IIA of the periodic table (e.g. Mg, Ca, Sr, or Ba), a is 0 to about 20, b is 0 to about 20, c is 0 to about 20, d is 0 to about 20, and x is stoichiometrically required amount of oxygen to balance the metals, wherein at least two of a, b, c, and d independently is greater than 0, and with the proviso that Formula (A) excludes $CuV_2O_6$, $Cu_2V_2O_7$, $MoO_3$—$V_2O_5$, and $Nb_2O_5$—$V_2O_3$.

In an embodiment, a process for preparing a heterogeneous catalyst comprising a mixed metal oxide according to Formula (A) $Mo_aV_bNb_cQ_dO_x$ (A), wherein Q is Ce, Cu, or Sn, an element selected from Group IA of the periodic table (e.g. Na, K or Cs), or an element selected from Group IIA of the periodic table (e.g. Mg, Ca, Sr, or Ba), a is 0 to about 20, b is 0 to about 20, c is 0 to about 20, d is 0 to about 20, and x is stoichiometrically required amount of oxygen to balance the metals, wherein at least two of a, b, c, and d independently is greater than 0, and with the proviso that Formula (A) excludes $CuV_2O_6$, $Cu_2V_2O_7$, $MoO_3$—$V_2O_5$, and $Nb_2O_5$—$V_2O_3$; the process comprises preparing the mixed metal oxide according to Formula (A) by dissolution and spray drying of metal salts, or a coprecipitation process, or an impregnation process, or a combination comprising at least one of the foregoing processes.

In an embodiment, a method for preparing a diaryl carbonate comprises transesterifying diethylcarbonate with an aromatic hydroxy compound in the presence of a heterogeneous catalyst comprising a mixed metal oxide according to Formula (A) $Mo_aV_bNb_cQ_dO_x$ (A) wherein Q is Ce, Cu, Sn, an element selected from Group IA of the periodic table, or an element selected from Group IIA of the periodic table, a is 0 to about 20, b is 0 to about 20, c is 0 to about 20, d is 0 to about 20, and x is stoichiometrically required amount of oxygen to balance the metals, wherein at least two of a, b, c, and d independently is greater than 0, and with the proviso that Formula (A) excludes $CuV_2O_6$, $Cu_2V_2O_7$, $MoO_3$—$V_2O_5$, and $Nb_2O_5$—$V_2O_3$.

In an embodiment, a method for preparing a diaryl carbonate comprises transesterifying diethylcarbonate with an aromatic hydroxy compound in the presence of a heterogeneous catalyst comprising a mixed metal oxide according to Formula (A) $Mo_aV_bNb_cQ_dO_x$ (A) wherein Q is Ce, Cu, Sn, an element selected from Group IA of the periodic table, or an element selected from Group IIA of the periodic table, a is 0 to about 20, b is 0 to about 20, c is 0 to about 20, d is 0 to about 20, and x is stoichiometrically required amount of oxygen to balance the metals, wherein at least two of a, b, c, and d independently is greater than 0, and with the proviso that Formula (A) excludes $CuV_2O_6$, $Cu_2V_2O_7$, $MoO_3$—$V_2O_5$, and $Nb_2O_5$—$V_2O_3$.

The above described and other features are exemplified by the following figures and detailed description.

BRIEF DESCRIPTION OF THE DRAWINGS

The following is a brief description of the drawings which are presented for the purposes of illustrating the exemplary embodiments disclosed herein and not for the purposes of limiting the same.

DETAILED DESCRIPTION

Disclosed herein are new mixed metal oxide catalysts suitable as heterogeneous catalysts for catalyzing the transesterification process of aromatic hydroxy compounds with a dialkyl carbonate to form aromatic carbonates. The heterogeneous catalyst comprises a combination of two, three, four, or more oxides of Mo, V, Nb, Ce, Cu, Sn, an element selected from Group IA of the periodic table (e.g. Na, K or Cs), or an element selected from Group IIA of the periodic table (e.g. Mg, Ca, Sr, or Ba). The combination of these metal oxides provides a transesterification catalyst with high activity which is capable of achieving nearly 100 percent (%) selectivity in the transesterification reaction. High activity of the catalyst leads to a higher reaction rate and a shorter time to reach equilibrium. Commercially this is advantageous as it results in increased throughput of the reactor and hence higher productivity.

In an embodiment, the general formula for the mixed metal oxide of the heterogeneous catalyst is according to Formula (A)

$$Mo_aV_bNb_cQ_dO_x \quad (A)$$

wherein
Q is
Ce, Cu, Sn,
an element selected from Group IA of the periodic table (e.g. Na, K or Cs), or
an element selected from Group IIA of the periodic table (e.g. Mg, Ca, Sr, or Ba);
a is 0 to about 20, specifically about 0.01 to about 10, and more specifically about 0.1 to about 5;
b is 0 to about 20, specifically about 0.05 to about 10, and more specifically about 0.1 to about 6;
c is 0 to about 20, specifically about 0.01 to about 20, more specifically about 0.05 to about 15, and yet more specifically about 0.1 to about 10;
d is 0 to about 20, specifically about 0.01 to about 10, and more specifically about 0.1 to about 5; and
x is stoichiometrically required amount of oxygen to balance the metals; wherein at least two of a, b, c, and d independently is greater than 0; and with the proviso that Formula (A) excludes $CuV_2O_6$, $Cu_2V_2O_7$, $MoO_3$—$V_2O_5$, and $Nb_2O_5$—$V_2O_3$.

In an embodiment, Formula (A) is $$Mo_aV_bNb_cQ_dO_x \quad (A)$$

wherein
Q is Ce, Cu, Sn, an element selected from Group IA of the periodic table (e.g. Na, K or Cs), or an element selected from Group IIA of the periodic table (e.g. Mg, Ca, Sr, or Ba);
a is 0 to about 20, specifically about 0.01 to about 10, and more specifically about 0.1 to about 5;
b is 0 to about 20, specifically about 0.05 to about 10, and more specifically about 0.1 to about 6;
c is 0 to about 20, specifically about 0.01 to about 20, more specifically about 0.05 to about 15, and yet more specifically about 0.1 to about 10;
d is 0 to about 20, specifically about 0.01 to about 10, and more specifically about 0.1 to about 5; and
x is stoichiometrically required amount of oxygen to balance the metals; wherein at least three of a, b, c, and d independently is greater than 0.

In an embodiment, Formula (A) is $$Mo_aV_bNb_cQ_dO_x \quad (A)$$

wherein
Q is Ce, Cu, or Sn;
a is 0 to about 20, specifically about 0.01 to about 10, and more specifically about 0.1 to about 5;
b is 0 to about 20, specifically about 0.05 to about 10, and more specifically about 0.1 to about 6;
c is 0 to about 20, specifically about 0.01 to about 20, more specifically about 0.05 to about 15, and yet more specifically about 0.1 to about 10;
d is 0 to about 20, specifically about 0.01 to about 10, and more specifically about 0.1 to about 5; and
x is stoichiometrically required amount of oxygen to balance the metals; wherein at least two of a, b, c, and d independently is greater than 0; and with the proviso that Formula (A) excludes $CuV_2O_6$, $Cu_2V_2O_7$, $MoO_3$—$V_2O_5$, and $Nb_2O_5$—$V_2O_3$.

In an embodiment, Formula (A) is $$Mo_aV_bNb_cQ_dO_x \quad (A)$$

wherein
Q is an element selected from Group IA of the periodic table (e.g. Na, K or Cs);
a is 0 to about 20, specifically about 0.01 to about 10, and more specifically about 0.1 to about 5;
b is 0 to about 20, specifically about 0.05 to about 10, and more specifically about 0.1 to about 6;
c is 0 to about 20, specifically about 0.01 to about 20, more specifically about 0.05 to about 15, and yet more specifically about 0.1 to about 10;
d is 0 to about 20, specifically about 0.01 to about 10, and more specifically about 0.1 to about 5; and
x is stoichiometrically required amount of oxygen to balance the metals; wherein at least two of a, b, c, and d independently is greater than 0; and with the proviso that Formula (A) excludes $CuV_2O_6$, $Cu_2V_2O_7$, $MoO_3$—$V_2O_5$, and $Nb_2O_5$—$V_2O_3$.

In an embodiment, Formula (A) is $$Mo_aV_bNb_cQ_dO_x \quad (A)$$

wherein
Q is an element selected from Group IIA of the periodic table (e.g. Mg, Ca, Sr, or Ba);
a is 0 to about 20, specifically about 0.01 to about 10, and more specifically about 0.1 to about 5;
b is 0 to about 20, specifically about 0.05 to about 10, and more specifically about 0.1 to about 6;
c is 0 to about 20, specifically about 0.01 to about 20, more specifically about 0.05 to about 15, and yet more specifically about 0.1 to about 10;
d is 0 to about 20, specifically about 0.01 to about 10, and more specifically about 0.1 to about 5; and
x is stoichiometrically required amount of oxygen to balance the metals; wherein at least two of a, b, c, and d independently is greater than 0; and with the proviso that Formula (A) excludes $CuV_2O_6$, $Cu_2V_2O_7$, $MoO_3$—$V_2O_5$, and $Nb_2O_5$—$V_2O_3$.

Exemplary mixed metal oxides according to Formula (A) include Mo—V—Cu oxides; Mo—V—Nb oxides; Mo—V—Nb—Ce oxides, Mo—V—Nb—Mg oxides; Mo—V—Nb—Cs oxides; Mo—V—Nb—Sn oxides; or Mo—V—Nb—Cu oxides.

The heterogeneous catalyst can be in the bound form using binders or supported on a solid support. In the supported embodiment, the mixed metal oxides can be deposited on porous solid supports including, for example, $SiO_2$, $ZrO_2$, $Al2O_3$, or $TiO_2$. For example, the solid supports can be ⅛" (3.175 mm) diameter cylindrical extrudates made of any of the above compounds with sufficient surface area and pore characteristics. The salt solution of active material (metals) can be used for impregnation of supports. Upon calcination the active material binds into the support via chemical linkages. Hence the support is a carrier to the active material. The high porosity and surface area aids to finely disperse the metal which enhances the activity per unit mass of active metal. One of ordinary skill in the art can carry these processes without undue experimentation.

The formed/bound heterogeneous catalyst can comprise a binder and the active mixed metal oxide material or a lubricant and the active mixed metal oxide material.

In an embodiment, the bound or formed catalysts can be made by an extrusion process with the use of a binder to form catalyst extrudates. The binder can be silica (e.g. colloidal silica, and the like), silica-based clays (e.g. kaolin; an Attapulgite-based clay such as Actigel™, which is a refined form of clay comprising of magnesium aluminum silicate, available from Active Minerals Inc., Georgia, USA; a magnesium aluminum silicate clay such as the MUG® variety of clays including MUG-200, MUG-400, etc. available from Active Minerals Inc., Georgia, USA; and the like), alumina, or a combination comprising at least one of the foregoing. The amount of binder that can be present in the extrudate can be about 10 to about 90 wt. % (dry basis) of the total weight of the extrudate, specifically about 20 to about 60 wt. % (dry basis), and more specifically about 30 to about 40 wt. % (dry basis). In an exemplary process, the binder is added to the active mixed metal oxide material and optional aqueous medium and extruded using an extruder. The shape of the extrudate is not particularly limited and can be cylindrical, hollow cylinders, lobes, and the like.

In another embodiment, the bound or formed catalysts can be prepared by tableting the mixed metal oxide with a lubricant, for example graphite. Within this embodiment, about 1 to about 5 wt. %, specifically about 2 to about 4 wt. %, and more specifically about 2.5 to about 3.5 wt. % lubricant is added to the active mixed metal oxide material and the mixture is tableted using a tableting machine, the amounts based on the total weight of the tablet. The lubricant is usually inert and does not contribute to the activity or selectivity of the catalyst.

The mixed metal oxides can be prepared by conventional methods, for example, metal salt dissolution and spray drying or co-precipitation techniques for bulk catalysts or by impregnation technique for supported catalysts, followed by drying and calcination. Combinations of one or more of these processes can be used.

In a general process, dissolution of salts can involve separately dissolving each metal salt and then mixing each of the solutions together at room temperature or at higher temperatures ranging from about 40 to about 90° C. The mixture can be stirred for an appropriate amount of time, for example about 10 to about 15 hours. The resulting liquid may or may not have any precipitates. The resulting mixture can be spray dried to obtain a homogeneous solid mixture.

Co-precipitation processes generally involve mixing the relevant salts of the metal oxides in a solvent, typically water, and allowing the mixed metal oxides to co-precipitate. Usually this is accomplished by addition of a base (e.g. ammonium hydroxide) which precipitates the metal hydroxides. The solids can be collected by filtration.

Impregnation processes generally involve contacting the dried support with a metal salt solution. The contacting of the solution can be either done in a drop by drop fashion or the support can be immersed in the solution. In the former case the addition of solution is stopped once the support is saturated with liquid, and is termed incipient wetness method. In the latter case the support can be immersed for times ranging from about 5 minutes to about 10 hours at room temperature up to about 60° C., specifically at temperatures from about 30 to about 60° C.

The drying step generally involves removal of unbound moisture from the catalyst. Drying can be accomplished using an oven at about 80 to about 120° C., specifically about 110° C. for a period of about 6 to about 24 hours, more specifically about 8 to about 12 hours.

The calcination step generally involves heating in presence of air at temperatures of about 200° to about 750° C., specifically about 250° to about 600° C., and more specifically about 450° to about 550° C. During this step the metal salts or hydroxides are decomposed to form metal oxides. While calcining with a binder or catalyst on a support, the metal salts or hydroxides are decomposed to form metal oxides which are chemically linked to either the binder or to the support through an oxygen bond.

A process for preparing a mixed metal oxide according to Formula (A) $Mo_aV_bNb_cQ_dO_x$ (A) as described herein; the process comprises preparing the catalyst by dissolution and spray drying or a coprecipitation process, an impregnation process, or both.

The heterogeneous catalyst can be used in the process for the production of a diaryl carbonate comprising transesterifying a dialkyl carbonate with an aromatic hydroxy compound in the presence of the heterogeneous catalyst to form an aryl alkyl carbonate, and further disproportionating or transesterifying with phenol the aryl alkyl carbonate in the presence of the catalyst to form a diaryl carbonate.

Exemplary dialkyl carbonates include $C_1$-$C_6$ dialkylcarbonates, specifically $C_1$-$C_3$ dialkylcarbonates such as dimethyl carbonate, diethylcarbonate, and combinations comprising at least one of the foregoing.

Exemplary aromatic hydroxy compounds include phenol and substituted phenols such as a phenol containing a substituent of cyano group, aliphatic group, olefinic group, aromatic group, halogen, ester group, ether group, nitro group, or a combination comprising at least one of the foregoing. Exemplary substituted phenols include cresols, xylenols, p-cumylphenol, 4-nitrophenol, 2-chlorophenol, 4-chlorophenol, 2-acetylphenol, 4-acetylphenol, methyl salicylate, 4-methylcarboxyphenol, and the like. The aromatic hydroxy compound can have the formula (I)

(I)

wherein n is an integer 1 to 3 and each $R^1$ is independently a linear or branched, optionally substituted $C_{1-34}$ alkyl (specifically $C_{1-6}$ alkyl, more specifically $C_{1-4}$ alkyl), $C_{1-34}$ alkoxy (specifically $C_{1-6}$ alkoxy, more specifically $C_{1-4}$ alkoxy), $C_{5-34}$ cycloalkyl, $C_{7-34}$ alkylaryl $C_{6-34}$ aryl, a halogen radical (specifically a chlorine radical), or —C(=O)$OR^1$ wherein $R^1$ is H, linear or branched $C_{1-34}$ alkyl (specifically $C_{1-6}$ alkyl, more specifically $C_{1-4}$ alkyl), $C_{1-34}$ alkoxy (specifically $C_{1-16}$ alkoxy, specifically $C_{1-4}$ alkoxy), $C_{5-34}$ cycloalkyl, $C_{7-34}$ alkylaryl, or $C_{6-34}$ aryl.

The diaryl carbonate which can be prepared using the heterogeneous catalyst can be diphenyl carbonate, methylphenyl-phenyl carbonates or di-(methylphenyl) carbonates (wherein the methyl group can be in any desired position on the phenyl rings), dimethylphenyl-phenyl carbonates or di-(dimethylphenyl) carbonates (wherein the methyl groups can be in any desired position on the phenyl rings), chlorophenyl-phenyl carbonates and di-(chlorophenyl) carbonates (wherein the chloro group can be in any desired position on the phenyl rings), 4-ethylphenyl-phenyl carbonate, di-(4-ethylphenyl) carbonate, 4-n-propylphenyl-phenyl carbonate, di-(4-n-propylphenyl) carbonate, 4-isopropylphenyl-phenyl carbonate, di-(4-isopropylphenyl) carbonate, 4-n-butylphenyl-phenyl carbonate, di-(4-n-butylphenyl) carbonate, 4-isobutylphenyl-phenyl carbonate, di-(4-isobutylphenyl) carbonate, 4-tert-butylphenyl-phenyl carbonate, di-(4-tert-butylphenyl) carbonate, 4-n-pentylphenyl-phenyl carbonate, di-(4-npentylphenyl) carbonate, 4-n-hexylphenyl-phenyl carbonate, di-(4-n-hexylphenyl) carbonate, 4-isooctylphenyl-phenyl carbonate, di-(4-isooctylphenyl) carbonate, 4-n-nonylphenyl-phenyl carbonate, di-(4-n-nonyl-phenyl) carbonate, 4-cyclohexylphenyl-phenyl carbonate, di-(4-cyclohexylphenyl) carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl) carbonate, (1-naphthyl)-phenyl carbonate, (2-naphthyl)-phenyl carbonate, di-(1-naphthyl) carbonate, di-(2-naphthyl) carbonate, 4-(1-naphthyl)-phenyl-phenyl carbonate, 4-(2-naphthyl)-phenyl-phenyl carbonate, di-[4-(1-naphthyl)-phenyl] carbonate, di-[4-(2-naphthyl)phenyl] carbonate, 4-phenoxyphenyl-phenyl carbonate, di-(4-phenoxyphenyl) carbonate, 3-pentadecylphenyl-phenyl carbonate, di-(3-pentadecylphenyl) carbonate, 4-tritylphenyl-phenyl carbonate, di-(4-tritylphenyl) carbonate, methyl salicylate-phenyl carbonate, di-(methyl salicylate) carbonate, ethyl salicylate-phenyl carbonate, di-(ethyl salicylate) carbonate, n-propyl salicylate-phenyl carbonate, di-(n-propyl salicylate) carbonate, isopropyl salicylate-phenyl carbonate, di-(isopropyl salicylate) carbonate, n-butyl salicylate-phenyl carbonate, di-(n-butyl salicylate) carbonate, isobutyl salicylate-phenyl carbonate, di-(isobutyl salicylate) carbonate, tert-butyl salicylate-phenyl carbonate, di-(tert-butyl salicylate) carbonate, di-(phenyl salicylate)-carbonate, di-(benzyl salicylate) carbonate, or a combination comprising one or more of the foregoing.

In an embodiment, the diaryl carbonate is diphenyl carbonate, or a diaryl carbonate wherein one or both aryl groups have an electron-withdrawing substituents, for example bis (4-nitrophenyl)carbonate, bis(2-chlorophenyl)carbonate, bis (4-chlorophenyl)carbonate, bis(methyl salicyl)carbonate, bis(4-methylcarboxylphenyl) carbonate, bis(2-acetylphenyl) carboxylate, and bis(4-acetylphenyl) carboxylate.

In an embodiment, the heterogeneous catalyst is used in the transesterification process to produce diphenyl carbonate from phenol and a dialkyl carbonate.

A process of the production of a diaryl carbonate comprises transesterifying a dialkyl carbonate with an aromatic hydroxy compound in the presence of a heterogeneous catalyst according to the Formula (A) $Mo_aV_bNb_cQ_dO_x$ (A) wherein Q is Ce, Cu, or Sn, an element selected from Group IA of the periodic table (e.g. Na, K or Cs), or an element selected from Group IIA of the periodic table (e.g. Mg, Ca, Sr, or Ba), a is 0 to about 20, b is 0 to about 20, c is 0 to about 20, d is 0 to about 20, and x is stoichiometrically required amount of oxygen to balance the metals, wherein at least two or three of a, b, c, and d independently is greater than 0, and with the proviso that Formula (A) excludes $CuV_2O_6$, $Cu_2V_2O_7$, $MoO_3$—$V_2O_5$, and $Nb_2O_5$—$V_2O_3$.

In an embodiment, the heterogeneous catalyst comprises a mixed metal oxide according to Formula (A) $Mo_aV_bNb_cQ_dO_x$ (A) wherein Q is Ce, Cu, or Sn, an element selected from Group IA of the periodic table (e.g. Li, Na, K or Cs), or an element selected from Group IIA of the periodic table (e.g. Mg, Ca, Sr, or Ba), a is 0 to about 20, specifically about 0.01 to about 10, and more specifically about 0.1 to about 5; b is 0 to about 20, specifically about 0.05 to about 10, and more specifically about 0.1 to about 6; c is 0 to about 20, specifically about 0.01 to about 20, more specifically about 0.05 to about 15, and yet more specifically about 0.1 to about 10; d is 0 to about 20, specifically about 0.01 to about 10, and more specifically about 0.1 to about 5; x is stoichiometrically required amount of oxygen to balance the metals wherein at least two or three of a, b, c, and d independently is greater than 0; and with the proviso that Formula (A) excludes $CuV_2O_6$, $Cu_2V_2O_7$, $MoO_3$—$V_2O_5$, and $Nb_2O_5$—$V_2O_3$. Within this embodiment, the heterogeneous catalyst comprises a solid support (e.g. $SiO_2$, $ZrO_2$, $Al_2O_3$, or $TiO_2$) or comprises a binder (e.g. silica, including colloidal silica, clay including Attapulgite-based clay or a combination comprising at least one of the foregoing). Within these embodiments, the heterogeneous catalyst is in the form of a tablet or extrudate.

The combination of these metal oxides provides a transesterification catalyst with high activity and selectivity in the transesterification reaction.

The catalysts and their use are further illustrated by the following non-limiting examples.

EXAMPLES

Example 1. Mixed Metal Oxide Catalysts

Several mixed metal oxide catalysts were prepared by conventional co-precipitation techniques or by impregnation technique followed by overnight drying and calcination. The catalysts in Table 1 were prepared according to the procedures described below except Catalysts E and F were obtained from Sigma Aldrich™ (USA).

TABLE 1

| Catalyst | Catalyst Composition* | % PMC Yield/conversion at 15 minutes residence time |
|---|---|---|
| A | $Mo_1V_{0.3}Cu_{0.23}O_x$ | 6.8 |
| B | $Mo_1V_{0.3}Nb_{0.12}Cu_{0.23}O_x$ | 6.8 |
| C | $Mo_1V_5Nb_{15}O_x$ | 3.1** |
| D | $V_1Cu_{0.3}O_x$ | 4.6 |
| E | $VO_x$ | 3.9 |
| F | $MoO_x$ | 2.2 |
| G | $V_1Nb_{2.3}O_x$ | 2.2 |
| H | $Mo_1V_{0.3}Nb_{0.12}Ce_{0.23}O_x$ | 2.3 |
| I | $Mo_1V_{0.3}Nb_{0.12}Mg_{0.23}O_x$ | 4.2 |
| J | $Mo_1V_{0.3}Nb_{0.12}Cs_{0.23}O_x$ | 6.2 |
| P | $Mo_1V_{0.3}Nb_{0.12}Sn_{0.23}O_x$ | 4.3 |

*the subscript 'x' represents the stoichiometrically required amount of oxygen to balance the metals
**Data at 20 minutes Catalyst A: 60.2 grams (g) of $(NH_4)_6Mo_7O_{24} \cdot 4H_2O$ was added to 480 milliliters (ml) of deionized (DI) water. After dissolution 12.0 g of $NH_4VO_3$ was added and dissolved by heating to 70° C. The solution was cooled to ~40° C. to form Solution A. 19 g $Cu(NO_3)_2 \cdot 3H_2O$ was added to 60 ml of water and dissolved to form Solution B. Solution B was added to A slowly with stirring. The solution was spray dried and the solids were dried overnight at 110° C. followed by calcination at 550° C. in air.

Catalyst B: 120 g of $(NH_4)_6Mo_7O_{24} \cdot 4H_2O$ was dissolved in 700 ml deionized (DI) water. Once this was dissolved 24 g of $NH_4VO_3$ was added to the solution and dissolved by heating and stirring at 60-70° C. The solution was cooled to 40° C. and designated as Solution A. In a separate beaker 38 g of $Cu(NO_3)_2 \cdot 3H_2O$ was dissolved in 120 ml of DI water at room temperature. This solution was designated as Solution B. In another beaker 63 g of oxalic acid was added to 390 ml water. To that solution 14 g of Niobic acid was added. The resulting slurry was heated for 1 hour (h) at 90-100° C. and subsequently cooled to 30° C. This was designated as Solution C. Solution B was added to Solution A and stirred for 30 minutes (min). This was designated as Solution D. Solution C was added slowly (dropwise) to Solution D with stirring. The solution was spray dried after stirring overnight. The solids were dried overnight at 110° C. followed by calcination at 600° C. in air.

Catalyst C: Solution of 3.1 g of $(NH_4)_6Mo_7O_{24} \cdot 4H_2O$ and 11.0 g of $NH_4VO_3$ in DI water were made by dissolving and heating the metal salts in DI water at 70° C. 39 g of $Nb_2O_5$ was added into the above solution. The excess water was evaporated by heating with stirring at 70° C. The remaining solids were dried at 110° C. overnight and calcined at 450° C. in air for 4 h.

Catalyst D: 137 g of oxalic acid was added to 1000 ml of DI water and heated to 80° C. 105.5 g of ammonium metavanadate ($NH_4VO_3$) was added to the above solution with stirring. Once the $NH_4VO_3$ was dissolved the solution was cooled to <50° C. 25 g of basic copper carbonate ($CuCO_3Cu(OH)_2$) was added to the above solution. The solution was stirred overnight at 45° C. followed by spray drying. The solids were dried overnight at 110° C. followed by calcination at 550° C. in air.

Catalyst G: 11.5 g of $NH_4VO_3$ was dissolved in 300 ml of DI water by heating to 70° C. 31 g of $Nb_2O_5$ was added into the above solution. The excess water was removed in a rotavaporator by maintaining stirring at 70° C. The solids were filtered and dried at 110° C. overnight. These were calcined in air at 450° C. for 4 h.

Catalyst H: 80 g of $(NH_4)_6Mo_7O_{24} \cdot 4H_2O$ was dissolved in 600 ml DI water. 16 g of $NH_4VO_3$ was added to the above solution and dissolved by heating and stirring at 65-70° C. The solution was cooled to 40° C. to form Solution A. Solution B: In a separate beaker 43.5 g of $Ce(NO_3)_3 \cdot 6H_2O$ was added to 250 ml of DI water and dissolved at room temperature. Solution C: 40 g of oxalic acid solution was made with 300 ml water. To the above solution 9.2 g of Niobic acid was added. The resulting slurry was heated for 1 h at 90-95° C. and cooled to 30° C. Solution D: Solution B was added to Solution A at approximately 35-40° C. Stirring was continued for 30 min. Subsequently, Solution C was added slowly (dropwise) to solution D with stirring. After stirring overnight at room temperature, the solution was spray dried followed by drying in an oven at 110° C. overnight followed by calcination at 550° C. for 6 h in air.

Catalyst I: 80 g of $(NH_4)_6Mo_7O_{24} \cdot 4H_2O$ was dissolved in 600 ml DI water. 16 g of $NH_4VO_3$ was added to the above solution and dissolved by heating and stirring at 65-70° C. The solution was cooled to 40° C. to form Solution A. Solution B: In a separate beaker 25.6 g of $Mg(NO_3)_2 \cdot 6H_2O$ was added to 250 ml of DI water and dissolved at room temperature. Solution C: 40 g of oxalic acid solution was made with 300 ml water. To the above solution 9.2 g of Niobic acid was added. The resulting slurry was heated for 1 h at 90-95° C. and cooled to 30° C. Solution D: Solution B was added to Solution A at approximately 35-40° C. Stirring was continued for 30 min. Subsequently, Solution C was added slowly (drop-wise) to solution D with stirring. After stirring overnight at room temperature, the solution was spray dried followed by drying in an oven at 110° C. overnight followed by calcination at 550° C. for 6 h in air.

Catalyst J: 80 g of $(NH_4)_6Mo_7O_{24} \cdot 4H_2O$ was dissolved in 600 ml DI water. 16 g of $NH_4VO_3$ was added to the above solution and dissolved by heating and stirring at 65-70° C. The solution was cooled to 40° C. to form Solution A. Solution B: In a separate beaker 19.5 g of $CsNO_3$ was added to 250 ml of DI water and dissolved at room temperature. Solution C: 40 g of oxalic acid solution was made with 300 ml water. To the above solution 9.2 g of Niobic acid was added. The resulting slurry was heated for 1 h at 90-95° C. and cooled to 30° C. Solution D: Solution B was added to Solution A at approximately 35-40° C. Stirring was continued for 30 min. Subsequently, Solution C was added slowly (dropwise) to solution D with stirring. After stirring overnight at room temperature, the solution was spray dried followed by drying in an oven at 110° C. overnight followed by calcination at 550° C. for 6 h in air.

Catalyst P: 40 g of $(NH_4)_6Mo_7O_{24} \cdot 4H_2O$ was dissolved in 600 ml DI water. 8 g of $NH_4VO_3$ was added to the above solution and dissolved by heating and stirring at 65-70° C. The solution was cooled to 40° C. to form Solution A. Solution B: 21 g of oxalic acid solution was made with 200 ml water. To the above solution 4.6 g of Niobic acid was added. The slurry was heated for 1 h at 90-95° C. and cooled to 30° C. Solution C: 11 g of Tin oxalate was made into a suspension in 80 ml of water. Solution B was added to Solution A at approximately 35-40° C. Stirring was continued for 30 min. Solution C was added the above resulting in a precipitate. The solution was stirred overnight at room temperature and was evaporated to dryness in a roto-evaporator followed by drying and calcination at 600° C. for 5 h.

Figure 1:
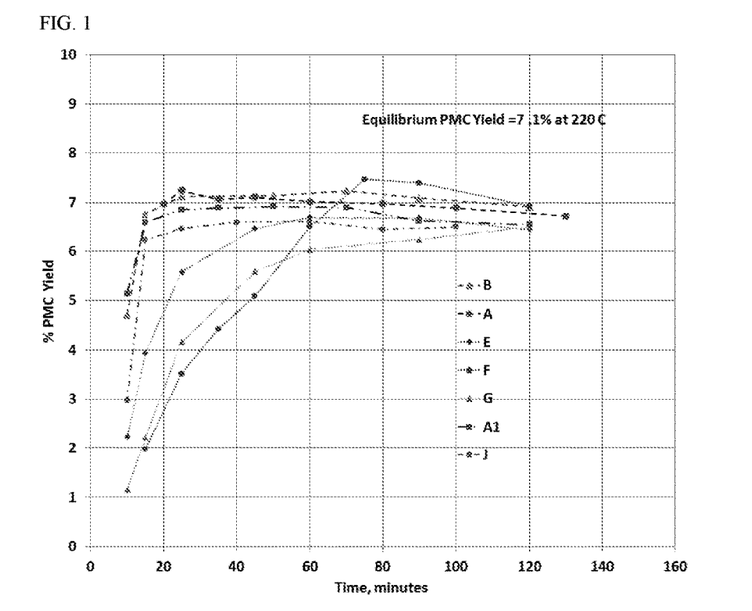
FIG. 1 is a graph of the performance comparison between heterogeneous catalysts A, B and J and comparative catalysts E, F, and G in the transesterification reaction of phenol and DMC to yield PMC.
Figure 2:
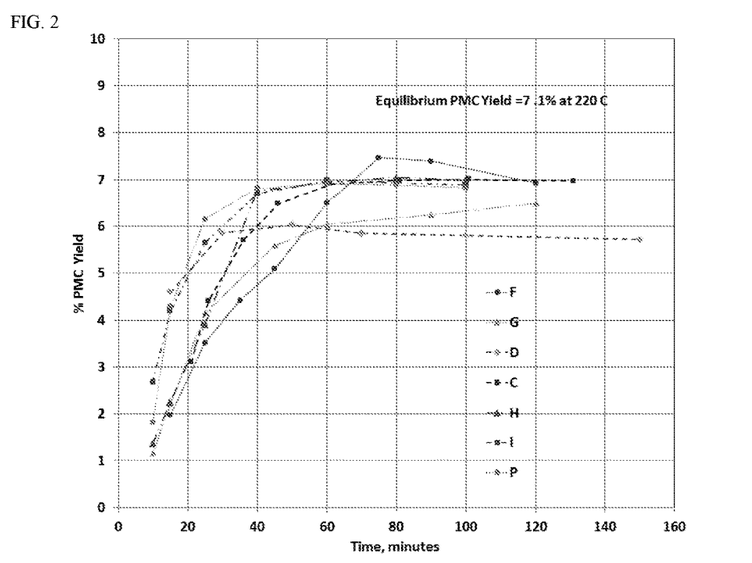
FIG. 2 is a graph of the performance comparison between heterogeneous catalysts C, D, H, I, and P and comparative catalysts F and G in the transesterification reaction of phenol and DMC to yield PMC.

The catalysts in Table 1 were individually tested in a batch reactor in a slurry mode under identical conditions. The temperature was 220° C. at autogenous pressure (~185 psig or 13.5 bar), molar DMC:Phenol=2. FIG. 1 and FIG. 2 show the performance of calcined catalysts A, B, C, D, J, H, I, and P in comparison to conventional catalysts E, F, and G reported in the literature.

The maximum achievable conversion or yield (at 100% selectivity) is 7.1% at 220° C. according to thermodynamics (equilibrium phenylmethylcarbonate (PMC) yield=7.1% at 220° C.). The yield/conversion at fifteen minutes for each catalyst is provided in Table 1.

As seen in FIG. 1 and Table 1 for a residence time or batch reaction time of 15 minutes, the yield or conversion achieved with catalyst A and B is 6.8% which is a 74% increase over the results of catalyst E at 3.9%. Comparison of performance of A and B in terms of yield or conversion with F (2.2%) and G (2.2%) gives a 3 fold increase (200% increase). Catalysts A and B reached equilibrium in 20 minutes. For a residence time of 15 minutes, the yield or conversion achieved with catalyst J is 6.2% which is a 59% increase over the results of catalyst E at 3.9%. A1 shown in FIG. 1 is a repetitive run of catalyst A. Catalysts E, F, and G reached maximum yield at 60 minutes or greater. After reaching equilibrium at 20 minutes, the yield or conversion values of A and B remain constant indicating insignificant decomposition of products. This fast approach to equilibrium of catalysts A, B, and J is a direct indication of their high activity which in turn increases the reaction rate. Based on the data, addition of elements Cu, Cu and Nb, or Cs and Nb to a mixed Mo—V oxide increased the transesterification rate.

From FIG. 2 and Table 1 it can be observed that the yield of catalyst D (4.6%) is double that of catalysts G and F (2.2%) at the 15 minutes residence time. However, the performance of catalyst C beyond 20 minutes was better than D, F, or G.

From FIG. 2 and Table 1 it can be observed that the yield of catalyst I (4.2%) and P (4.3%) is 90% higher than G and F (2.2%) at the 15 minutes residence time. In addition Catalysts I, H, and P reached near equilibrium PMC yield values (6.7%) at 40 minutes when compared to other catalysts C, D, F and G.

From the results in FIG. 1 and FIG. 2, it was found that the addition of Cu or Cs to mixed Mo—V—Nb-oxides or Mo—V-oxides significantly increases the reaction rate and hence transesterification equilibrium is reached within 20 minutes. It was also found that the addition of Sn or Ce or Mg to mixed Mo—V—Nb-oxides or Mo—V-oxides increases the reaction rate and hence transesterification equilibrium is reached within 40 minutes when compared to conventional catalysts like $V_2O_5$ or $MoO_3$ or V—Nb oxides. Moreover, the catalysts were found to be stable as reported in FIG. 1. The comparative catalysts took more than 60 minutes to reach equilibrium or maximum yield. Catalyst C also has high activity compared to comparative catalysts F and G although the maximum yield achieved was less than the equilibrium yield.

Example 2. Mo—V-Oxide Catalytic Systems with Varying Additives

Several Mo—V-oxide catalyst systems were prepared containing different additives as set out in Table 2.

TABLE 2

| Catalyst | Catalyst Composition* | % PMC Yield/conversion at 15 minutes residence time |
|---|---|---|
| K | $Mo_1V_{0.3}Nb_{0.05}Sb_{0.15}Ga_{0.03}O_x$ | 2.4 |
| L | $Mo_1V_{0.3}Nb_{0.12}Te_{0.23}O_x$ | 1.1 |
| M | $Mo_1V_{0.05}Cu_{0.07}P_{0.02}O_x$ | 2.6 |

TABLE 2-continued

| Catalyst | Catalyst Composition* | % PMC Yield/conversion at 15 minutes residence time |
|---|---|---|
| N | $Mo_1V_{0.3}Cu_{0.12}Ag_{0.23}O_x$ | 4.5 |
| O | $Mo_1V_{0.3}Nb_{0.12}Mn_{0.23}O_x$ | 2.1 |

*the subscript 'x' represents the stoichiometrically required amount of oxygen to balance the metals The catalysts in Table 2 were prepared according to the procedures described below.

Catalyst K: 8 g of $NH_4VO_3$ was dissolved in 170 ml of DI water followed by addition of Antimony oxide. The resulting mixture was heated at 96-100° C. with $N_2$ purge for 4 h. The mixture was cooled in a $N_2$ atmosphere. 40 g of $(NH_4)_6Mo_7O_{24}\cdot4H_2O$ was then added. A Niobium oxalate solution was prepared by adding 7 g of niobium oxalate in water and was added followed by 0.6 g of gallium oxide in 20 ml water. The final mixture was stirred and spray dried. The solution was spray dried followed by drying of solids overnight at 110° C. followed by calcination at 600° C. in air.

Catalyst L: 40 g of $(NH_4)_6Mo_7O_{24}\cdot4H_2O$ was dissolved in 655 ml DI water. Once this was dissolved 8 g of $NH_4VO_3$ was added to the above solution and dissolved by heating and stirring at 60-70° C. 12 g of Telluric acid dihydrate was added and dissolved to the above solution. The solution was cooled to 40° C. to result in Solution A. In another beaker 17 g of niobium oxalate was added into 160 ml water. This was designated as Solution B. Solution B was added to Solution A and stirred overnight. The final solution was dried using a rotary evaporator followed by drying of solids overnight at 110° C. followed by calcination at 600° C. in air.

Catalyst M: 50.1 g of $MoO_3$, 3.2 g of $V_2O_5$ and 2.8 g of CuO were added to 350 ml of DI water. The slurry was refluxed at 100° C. for 20 minutes. 4 g of aqueous phosphoric acid (85 wt. %) was added in 3 aliquots. The resulting mixture was refluxed for next 16 h. After 16 h all precursor solids were dissolved. The remaining liquid was evaporated to give an orange yellow powder. The solids were dried at 120° C. in $N_2$ for 12 h, followed by calcination at 300° C. in air.

Catalyst N: 40 g of $(NH_4)_6Mo_7O_{24}\cdot4H_2O$ was dissolved in 400 ml DI water. Once this is dissolved 8 g of $NH_4VO_3$ was added to the above solution and dissolved by heating and stirring at 60-70° C. The solution was cooled to 40° C. to form Solution A. In another beaker 21 g of oxalic acid was added to 160 ml DI water to make a solution designated as solution B. In a separate beaker 7 g of $Cu(NO_3)_2\cdot3H_2O$ was added to 40 ml of DI water and dissolved at room temperature. This was designated as Solution C. In another beaker 9 g of silver nitrate was dissolved in 40 ml of water and was designated as Solution D. Solution B was added to Solution A followed by Solution C. Following that Solution D was added to the mixture and stirred overnight. The solution was spray dried followed by drying of solids overnight at 110° C. followed by calcination at 600° C. in air.

Catalyst O: 80 g of $(NH_4)_6Mo_7O_{24}\cdot4H_2O$ was dissolved in 600 ml DI water. 16 g of $NH_4VO_3$ was added to the above solution and dissolved by heating and stirring at 65-70° C. The solution was cooled to 40° C. and designated Solution A. Solution B: In a separate beaker 25 g of $Mn(NO_3)_2\cdot4H_2O$ was added to 150 ml of DI water and dissolved at room temperature. Solution C: 40 g of oxalic acid solution was made with 300 ml water. To that 9.2 g of Niobic acid was added. The resulting slurry was heated for 1 h at 90-95° C. and cooled to 30° C. Solution D: Solution B was added to Solution A at approximately 35-40° C. The resulting solution was stirred for 30 min. Solution C was added slowly (dropwise) to solution D with stirring. The final solution was spray dried after stirring overnight at room temperature. Once spray dried, the powder was dried in an oven overnight at 110° C. followed by calcination at 550° C. for 6 h.

Figure 3:
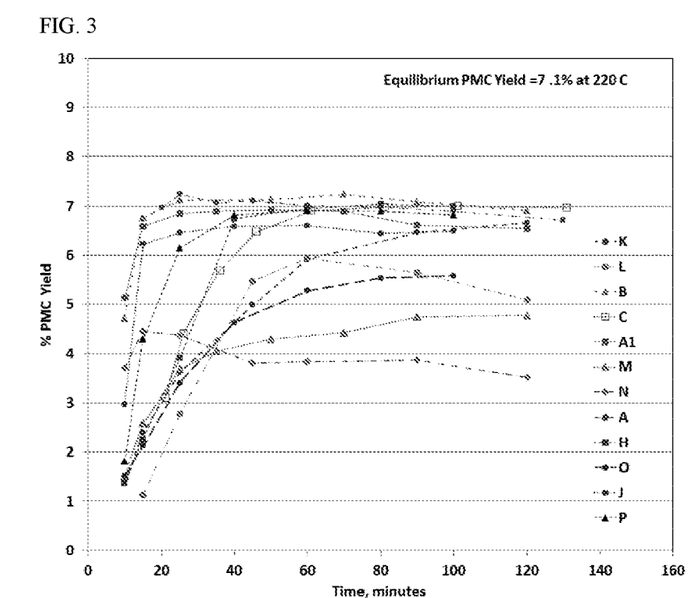
FIG. 3 is a graph of the time evolution of PMC yield for different additives to a Mo—V oxide catalytic system.

The catalysts in Table 2 were individually tested in a batch reactor in a slurry mode under identical conditions as set out in Example 1. The yield/conversion at fifteen minutes for each catalyst is provided in Table 2. FIG. 3 shows the performance of several of the calcined catalysts including K—O. The results show that addition of Cu improved the activity in comparison to other additives.

Example 3. Formed (Bound) Catalysts

The catalyst materials of Examples 1 and 2 can be formed into shapes, for example as cylindrical extrudates by mixing them with appropriate binders or tablets by mixing them with appropriate lubricants. The use of binders may prevent the leaching of the active material from the shaped catalyst. Suitable binders include clays that are naturally occurring or precipitated or fumed silica varieties or a combination comprising at least one of the foregoing. Table 3 the performance in a batch reactor test similar to Example 1 of sized extrudates (cylindrical extrudates crushed and sieved to particle size of less than 80 mesh number (<80 mesh#)) made from active material and different binders or binder compositions. The binders include MUG-MB™ ("Min-U-Gel"), a processed clay that comprises magnesium aluminum silicate and is available from Active Minerals Inc., Georgia, USA; Ludox AS-30™, a colloidal silica (30 wt. % suspension in water available from Sigma-Aldrich); Davisil-643™, a high-purity grade silica gel (pore size 150 angstroms, 200-425 mesh available from Sigma-Aldrich); and Kaolin™, a clay (aluminum silicate hydroxide available from Sigma-Aldrich). The weight percentages and crush strengths measured in pound per millimeter (lb/mm) are given in parenthesis.

TABLE 3

| Time Minutes | $Mo_1V_{0.3}Cu_{0.23}O_x$ (150 ml suspension) with binder MUG-MB™ (38 g) and Ludox AS-30 (33 g) (6.5 lb/mm) | $Mo_1V_{0.3}Nb_{0.12}Cu_{0.23}O_x$ (350 ml suspension) with binder MUG-MB™ (50 g) Davisil-643™ (15 g) and Ludox AS-30™ (14 g) (4.1 lb/mm) | $Mo_1V_{0.3}Cu_{0.23}O_x$ (150 ml suspension) with binder Kaolin™ (37 g), MUG-MB™ (20 g), and Ludox AS-30™ (16.5 g) (6.4 lb/mm) |
|---|---|---|---|
| 10 | 1.9 | 4 | 0 |
| 15 | 3.1 | 5.6 | 0 |
| 25 | 5.1 | 6.3 | 0 |
| 35 | 6 | 6.4 | 0 |
| 50 | 6.3 | 6.5 | 0.1 |
| 70 | 6.4 | 6.4 | 0.2 |
| 90 | 6.4 | 6.4 | 0.3 |
| 120 | 6.4 | 6.3 | 0.5 |

Notes:
$Mo_1V_{0.3}Cu_{0.23}O_x$ (150 ml suspension) was made from 45 g of $(NH_4)_6Mo_7O_{24}\cdot 4H_2O$, 9 g of $NH_4VO_3$, 14.3 g of $Cu(NO_3)_2\cdot 3H_2O$, and water followed by stirring and evaporation similar to preparation of Catalyst A.
$Mo_1V_{0.3}Nb_{0.12}Cu_{0.23}O_x$ (350 ml suspension) was made from 80.2 g of $(NH_4)_6Mo_7O_{24}\cdot 4H_2O$, 16 g of $NH_4VO_3$, and 25.2 g of $Cu(NO_3)_2\cdot 3H_2O$, 9.2 g of Niobic oxide hydrate, 41.3 g of oxalic acid and water followed by stirring and evaporation similar to preparation of Catalyst B.

It was observed that the sized extrudates from binders based on MUG-MB™ were performing significantly better than the sized extrudates made with the clay Kaolin™. The crush strengths of extrudates based on MUG-MB-MB™ and Kaolin™ clay binders were similar. The addition of porous silica Davisil-643™ decreases the crush strength of the extrudate but maintained the high yield and selectivity towards phenyl methyl carbonate. However the selectivity was 100% for sized extrudates with binders based on MUG-MB™ as well as Kaolin™.

Figure 4:
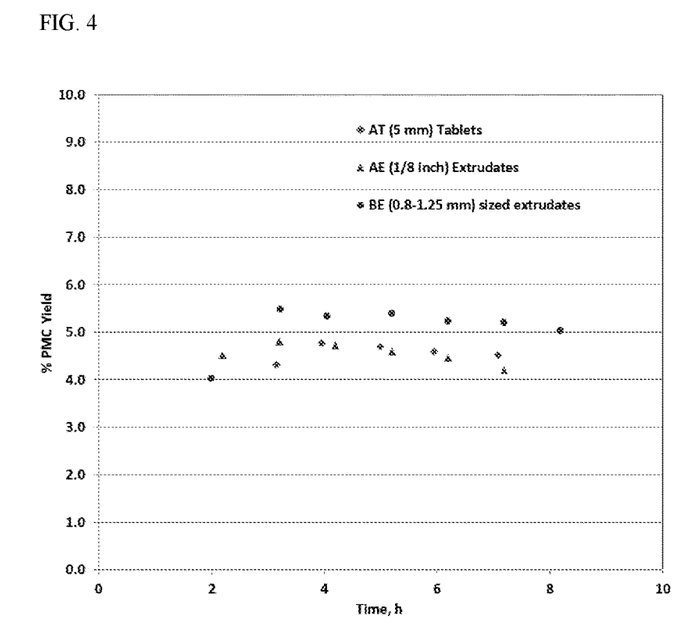
FIG. 4 is a graph of the steady state performance of formed (bound) catalysts in a continuous stirred tank reactor with catalysts AT, AE and BE.

FIG. 4 shows the steady state operation of bound catalysts in a continuous stirred tank reactor. The molar DMC to phenol ratio, temperature and pressure were similar to the batch reactor testing and is 2:1, 220° C., and autogenous pressure (pressure generated within the system) respectively. Table 4 explains the details of the bound catalysts tested in extrudate ("E") or tablet ("T") form, which is shown in FIG. 4.

TABLE 4

| Extrudate/Tablets | Binders/lubricants used | % Active material | WHSV, $h^{-1}$ |
|---|---|---|---|
| AT (5 mm/3.2 mm) | Graphite | 96 | 16 |
| AE (⅛") | MUG-MB™ and Ludox AS-30™ | 63 | 22 |
| BE (0.8-0.125 mm) | MUG-MB™ and Ludox AS-30™ and Davisil-643™ | 70 | 16 |

AE and BE: Extrudate made with catalyst A and B respectively.
AT: Tablet made with catalyst A
WHSV: Weight hourly space velocity, mass flow rate of reactants normalized by weight of the catalyst tested.

Set forth below are some embodiments of the catalyst, methods of making and using the catalyst disclosed herein.

Embodiment 1

A heterogeneous catalyst comprising a mixed metal oxide according to Formula (A): $Mo_aV_bNb_cQ_dO_x$ (A)
wherein
Q is Ce, Cu, Sn, an element selected from Group IA of the periodic table, or
an element selected from Group IIA of the periodic table,
a is 0 to about 20,
b is 0 to about 20,
c is 0 to about 20,
d is 0 to about 20, and
x is stoichiometrically required amount of oxygen to balance the metals,
wherein at least two of a, b, c, and d independently is greater than 0, and with the proviso that Formula (A) excludes $CuV_2O_6$, $Cu_2V_2O_7$, $MoO_3-V_2O_5$, and $Nb_2O_5-V_2O_3$.

Embodiment 2

The heterogeneous catalyst of Embodiment 1, wherein Q is Cu.

Embodiment 3

The heterogeneous catalyst of Embodiment 1, wherein Q is Ce.

Embodiment 4

The heterogeneous catalyst of Embodiment 1, wherein Q is Cs.

Embodiment 5

The heterogeneous catalyst of Embodiment 1, wherein Q is Mg.

Embodiment 6

The heterogeneous catalyst of Embodiment 1, wherein Q is Sn.

Embodiment 7

The heterogeneous catalyst of Embodiment 1, wherein Q is an element selected from Group IA of the periodic table.

Embodiment 8

The heterogeneous catalyst of Embodiment 1, wherein Q is an element selected from Group IIA of the periodic table.

Embodiment 9

The heterogeneous catalyst of Embodiment 1, comprising a Mo—V—Cu oxide, a Mo—V—Nb oxide, a Mo—V—Nb—Cu oxide, a Mo—V—Nb—Cs oxide, a Mo—V—Nb—Mg oxide, a Mo—V—Nb—Sn oxide, a Mo—V—Nb—Ce oxide, or a combination comprising at least one of the foregoing.

Embodiment 10

The heterogeneous catalyst of any one of the previous Embodiments, further comprising a porous solid support.

Embodiment 11

The heterogeneous catalyst of Embodiment 10, wherein the porous solid support is $SiO_2$, $ZrO_2$, $Al_2O_3$, or $TiO_2$.

Embodiment 12

The heterogeneous catalyst of any one of the previous Embodiments, further comprising a binder and prepared in the form of an extrudate; or further comprising a lubricant and prepared in the form of a tablet.

Embodiment 13

The heterogeneous catalyst of Embodiment 12, wherein the binder is present in the extrudate in an amount of about 10 to about 90 wt. % (dry basis) of the total weight of the extrudate; or wherein the lubricant is present in the tablet in an amount of about 1 to about 5 wt. % of the total weight of the tablet.

Embodiment 14

The heterogeneous catalyst of any of Embodiments 12-13, wherein the binder is silica, silica-based clay, magnesium aluminum silicate clay, alumina, or a combination comprising at least one of the foregoing.

Embodiment 15

The heterogeneous catalyst of any one of the previous Embodiments, wherein at least three of a, b, c, and d independently is greater than 0.

Embodiment 16

The heterogeneous catalyst of any one of the previous Embodiments, wherein a is greater than 0.

Embodiment 17

The heterogeneous catalyst of any one of the previous Embodiments, wherein b is greater than 0.

Embodiment 18

The heterogeneous catalyst of any one of the previous Embodiments, wherein c is greater than 0.

Embodiment 19

The heterogeneous catalyst of any one of the previous Embodiments, wherein d is greater than 0.

Embodiment 20

A method for preparing a heterogeneous catalyst comprising the mixed metal oxide of any one of the previous Embodiments, comprising preparing the mixed metal oxide according to Formula (A) by dissolution and spray drying or a coprecipitation process, an impregnation process, or a combination comprising at least one of the foregoing processes.

Embodiment 21

A method for preparing a diaryl carbonate, comprising: transesterifying a dialkyl carbonate with an aromatic hydroxy compound in the presence of the heterogeneous catalyst of any one of Embodiments 1-20.

Embodiment 22

The method of Embodiment 21, wherein the dialkyl carbonate is dimethyl carbonate; and wherein the aromatic hydroxy compound is phenol.

Embodiment 23

The method of Embodiment 21, wherein the dialkyl carbonate is diethyl carbonate; and wherein the aromatic hydroxy compound is phenol.

Embodiment 24

A diaryl carbonate prepared by the method of any one of Embodiments 21-24.

Embodiment 25

The diaryl carbonate of Embodiment 20, wherein the diaryl carbonate is diphenyl carbonate.

Embodiment 26

The use of the heterogeneous catalyst of any one of Embodiments 1-20 in a transesterification reaction of a dialkyl carbonate with an aromatic hydroxy compound to produce a diaryl carbonate.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. This Application claims priority to U.S. Application No. 61/871,888 filed on Aug. 30, 2013 and to U.S. Application No. 61/871,889 filed on Aug. 30, 2013, the contents of both of which are incorporated herein by reference in their entirety. "About" is intended to include the degree of error associated with measurement of the particular quantity based upon the equipment available at the time of filing the application.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A method for preparing a diaryl carbonate, comprising: transesterifying a dialkyl carbonate with an aromatic hydroxy compound in the presence of the heterogeneous catalyst wherein the heterogeneous catalyst comprises a mixed metal oxide according to Formula (A)

$$Mo_aV_bNb_cQ_dO_x \qquad (A)$$

wherein
Q is Cu, Sn, Mg or Cs
a is 0.1 to 5,
b is 0.5 to 6,
c is 0 to about 20,
d is 0.1 to 10, and
x is stoichiometrically required amount of oxygen to balance the metals,
wherein at least three of a, b, c, and d independently is greater than 0, and with the proviso that Formula (A) excludes $CuV_2O_6$, $Cu_2V_2O_7$, $MoO_3$—$V_2O_5$, and $Nb_2O_5$—$V_2O_3$.

2. The method of claim 1, wherein the dialkyl carbonate is dimethyl carbonate; and wherein the aromatic hydroxy compound is phenol.

3. The method of claim 1, wherein the dialkyl carbonate is diethyl carbonate; and wherein the aromatic hydroxy compound is phenol.

4. The method of claim 1, wherein Q is Cu.
5. The method of claim 1, wherein Q is Cs.
6. The method of claim 1, wherein Q is Mg.
7. The method of claim 1, wherein Q is Sn.
8. The method of claim 1, wherein the heterogeneous catalyst comprises a Mo—V—Cu oxide, a Mo—V—Nb—Cu oxide, a Mo—V—Nb—Cs oxide, a Mo—V—Nb—Mg oxide, a Mo—V—Nb—Sn oxide, or a combination thereof.

9. The method of claim 1, wherein the heterogeneous catalyst further comprises a binder and is prepared in the form of an extrudate.

10. The method of claim 9, wherein the binder is present in the extrudate in an amount of about 10 to about 90 wt. % (dry basis) of the total weight of the extrudate.

11. The method of claim 9, wherein the binder is silica, silica-based clay, magnesium aluminum silicate clay, alumina, or a combination thereof.

12. The method of claim 1, wherein the heterogeneous catalyst further comprises a lubricant and is prepared in the form of a tablet.

13. The method of claim 12, wherein the lubricant is present in the tablet in an amount of about 1 to about 5 wt. % of the total weight of the tablet.

14. The method of claim 12, wherein the heterogeneous catalyst further comprises a binder and wherein the binder is silica, silica-based clay, magnesium aluminum silicate clay, alumina, or a combination thereof.

* * * * *